United States Patent [19]

Tabakoff

[11] Patent Number: 4,528,295

[45] Date of Patent: Jul. 9, 1985

[54] COMPOSITION AND METHOD FOR REDUCING BLOOD ACETALDEHYDE LEVELS

[76] Inventor: Boris Tabakoff, RFD 2, Elizabeth, Ill. 61028

[21] Appl. No.: 523,397

[22] Filed: Aug. 15, 1983

[51] Int. Cl.³ .................. A61K 31/195; A61K 31/44
[52] U.S. Cl. .................................. 514/345; 514/562; 514/811
[58] Field of Search ............... 424/319, 263; 546/301; 562/559

[56] References Cited

U.S. PATENT DOCUMENTS 3,819,480  6/1974  Hochschild ........................ 424/309
4,053,589 10/1977  Gans et al. ........................ 424/319
4,237,118 12/1980  Howard ............................. 424/150
4,313,952  2/1982  Baldacci ........................... 424/263

OTHER PUBLICATIONS

Lindros et al. "Elevated Blood Acetaldehyde in Alcoholics with Accelerated Ethanol Elimination", Pharmacology Bichemistry & Behavior, vol. 13, Suppl; pp. 119–124 (1980).

Primary Examiner—Albert T. Meyers
Assistant Examiner—Joyce L. Morrison
Attorney, Agent, or Firm—Dressler, Goldsmith, Shore, Sutker & Milnamow, Ltd.

[57] ABSTRACT

A therapeutic composition for reducing blood acetaldehyde level in a patient comprises methionine and a physiologically tolerable carrier. Additionally, potassium citrate and Vitamin B6 may be present in the composition.

8 Claims, 4 Drawing Figures

FIG. 1. BIOCHEMICAL EFFECTS OF THE METABOLISM OF ETHANOL TO ACETALDEHYDE

FREE RADICAL FORMATION

FIG. 3.
ENZYMATIC AND NON-ENZYMATIC DEFENSE MECHANISMS AGAINST FREE RADICALS
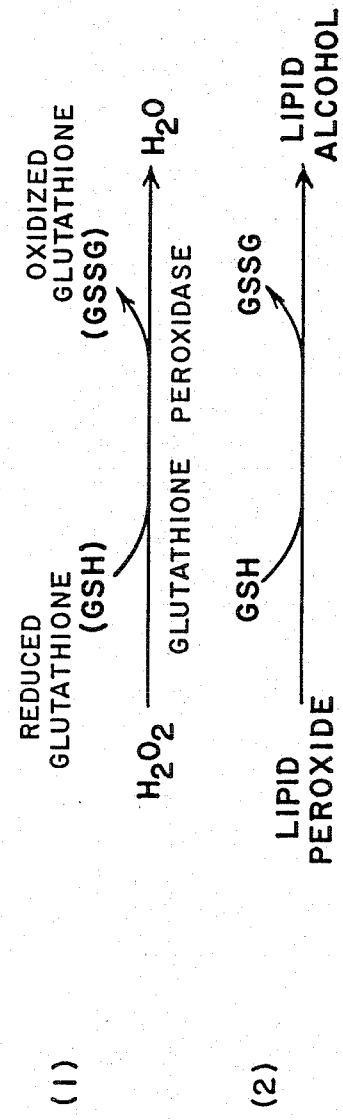
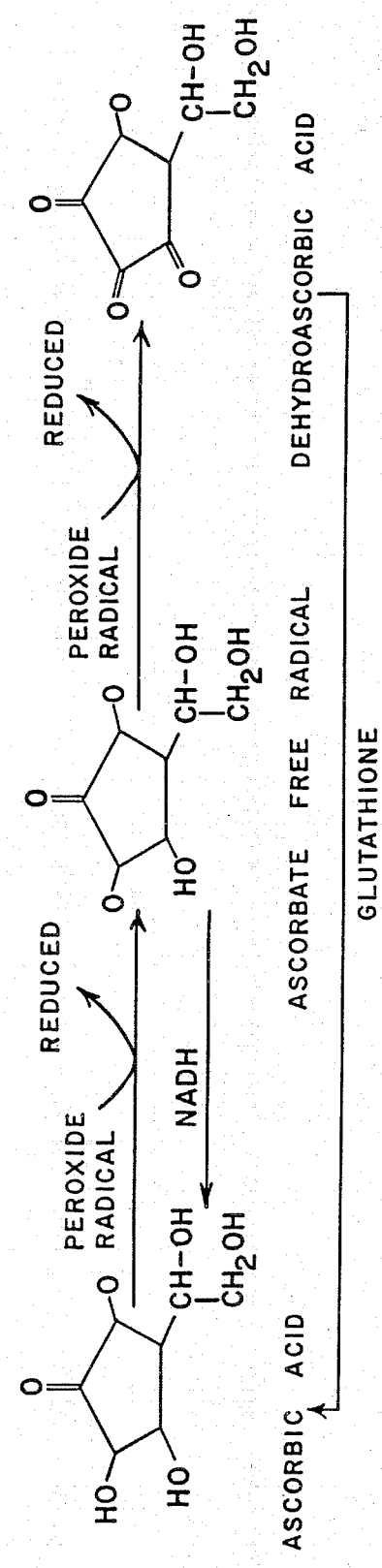

COMPOSITION AND METHOD FOR REDUCING BLOOD ACETALDEHYDE LEVELS

FIELD OF THE INVENTION

This invention relates to a composition and method for reducing blood acetaldehyde levels.

BACKGROUND OF THE INVENTION

Alcohol (ethanol or ethyl alcohol) is a product of the fermentative process and constitutes the active pharmacologic ingredient of beverages such as beer, wine and distilled spirits. The alcohol-containing beverages are widely used in most of the world's societies for their euphoric properties, to enhance the enjoyment of meals, and as social lubricants. Their use has been ingrained, particularly in Western societies, since pre-historic times, and the effects of alcohol, both positive and pathologic, have been recorded in the history and literature of every society and of every age. However, only during the last two to three decades has science taken up the challenge of trying to understand the mechanisms by which alcohol produces both its pleasurable as well as its damaging effects.

In particular, alcohol, through its metabolite, acetaldehyde, interferes in the body with the maintenance of proper circulating levels of pyridoxal phosphate, the active form of Vitamin B6 and essential for the conversion of methionine to cysteine. Cysteine, in turn, is important for the protection of the body from damage due to peroxides, free radicals and the aldehydes produced from ethanol or derived from other sources.

The present invention provides a composition and method of treatment that are effective in reducing blood acetaldehyde levels resulting from alcohol ingestion and the subsequent metabolism of ethanol.

SUMMARY OF THE INVENTION

The present invention contemplates a therapeutic preparation that includes methionine in an amount effective to reduce blood acetaldehyde level in a patient. Preferably potassium citrate and/or Vitamin B6 are also present in the preparation. This preparation is useful for treatment of some of the physiological manifestations of alcohol ingestion and also for reducing increase in blood acetaldehyde level attendant to administration of certain medication, e.g., calcium carbamide, disulfuram, metronidazale, tolbutamide, pargyline, or the like, especially in patients whose diet includes alcohol.

To treat elevated blood acetaldehyde levels, an effective amount of methionine is administered, usually orally or intravenously, to a patient in need of such treatment. A pharmaceutical unit dosage form of methionine can be provided in combination with pharmaceutical carriers which adapt methionine for systemic administration.

BRIEF DESCRIPTION OF THE DRAWINGS

In the drawings:

FIG. 3 is a schematic illustration of enzymatic and non-enzymatic defense mechanisms in animals against free radicals;

DESCRIPTION OF PREFERRED EMBODIMENTS

The active ingredient of the present composition is methionine, 2-amino-4-(methylthio)butyric acid, an essential amino acid. Both L- and D-forms of methionine are suitable; L-methionine is preferred, however.

While methionine is a naturally-occurring amino acid, the higher vertebrates are unable to synthesize it. Instead, the amount of methionine required for the normal functioning of the organism must be obtained from the diet.

The metabolism of alcohol in the liver and other tissues produces aldehydes and reduces the concentration of compounds which protect tissues from peroxides and free radicals. Aldehydes, in turn, also produce tissue damage. This damage is cumulative with a continuous use of alcohol. Also, in most tissues, the metabolism of alcohol terminates the normal metabolism of other foodstuffs. Thus, while alcohol is present in one's system, a metabolic imbalance prevails. This imbalance is rectified only after the elimination of alcohol from the system.

Figure 1:
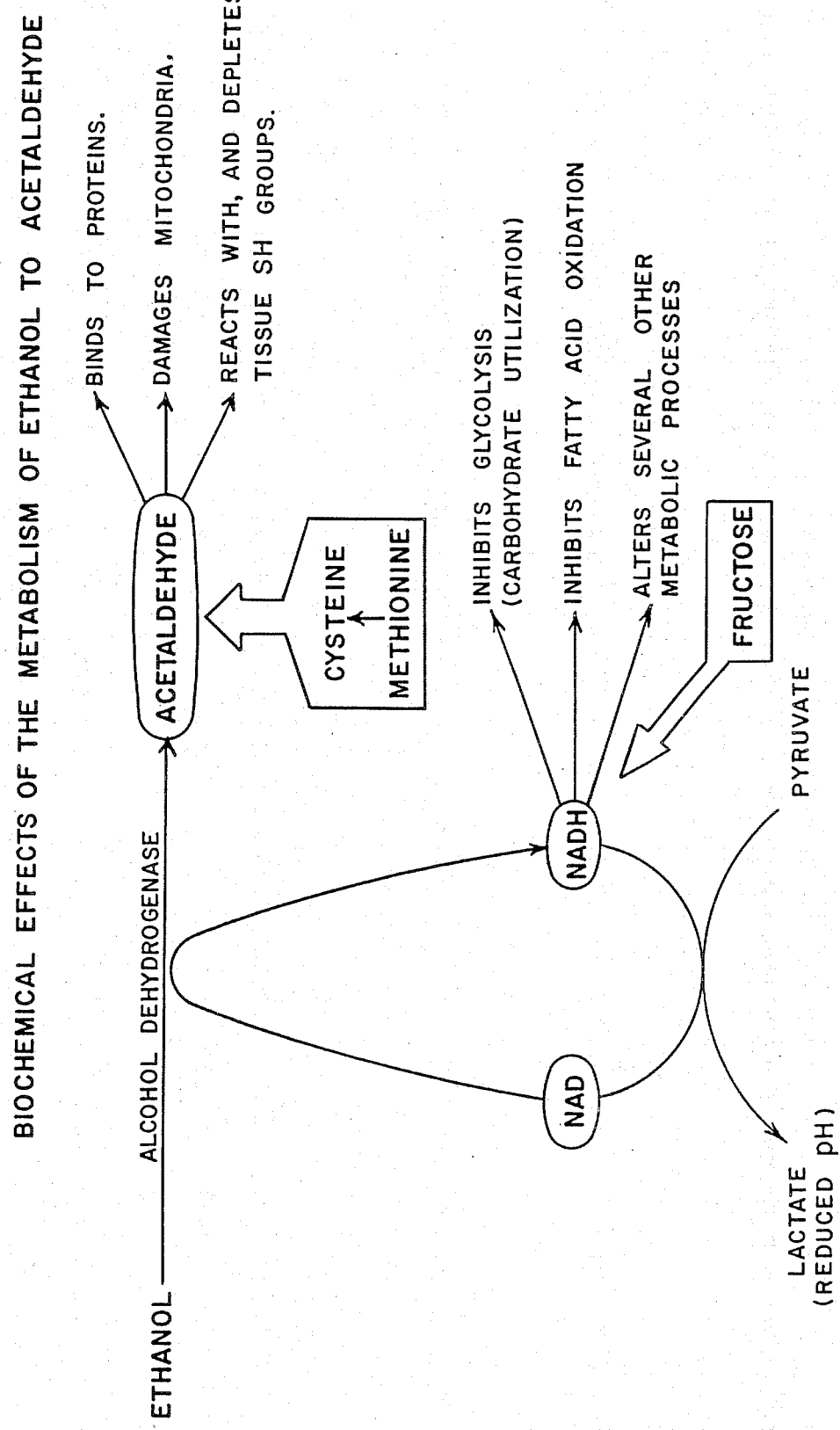
FIG. 1 is a schematic illustration of the biochemical conversion of alcohol to acetaldehyde and the known damaging effects produced by acetaldehyde and NADH (reduced nicotinamide adenine dinucleotide) generated by the metabolism of alcohol.
Figure 2:
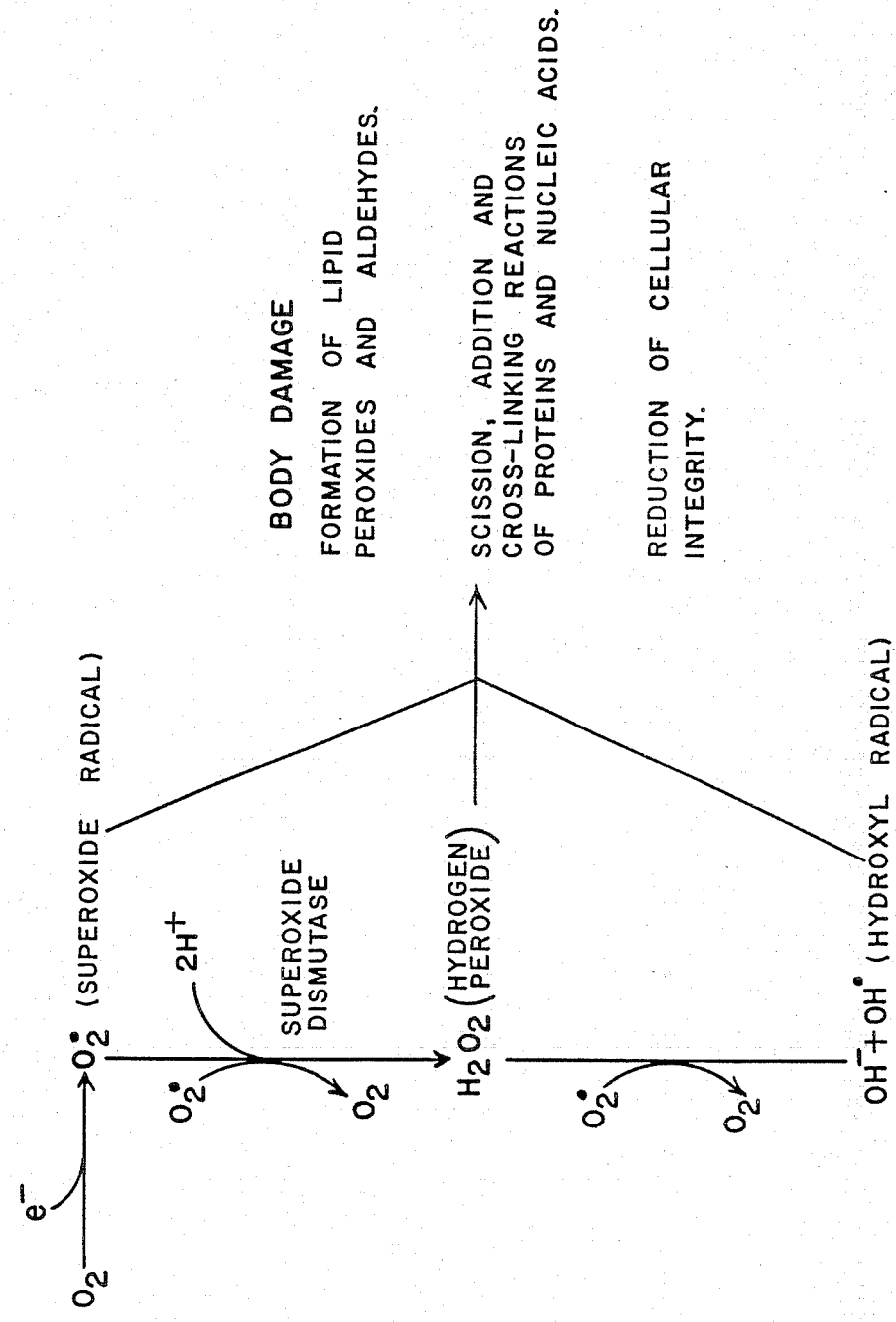
FIG. 2 is a schematic illustration of free radical formation and attendant damage upon ingestion of alcohol.

The biochemical effects of the metabolism of alcohol to acetaldehyde are schematically depicted in FIG. 1. Free radical formation and attendant, induced damage to the body are illustrated in FIG. 2. It has been found, however, that alcohol-induced damage to the stomach, intestine, and the liver can be prevented to a substantial degree by the administration of methionine.

Administration of a relatively large dose of methionine, preferably L-methionine, provides a controlled amount of cysteine needed by the individual who has ingested alcohol. The reason for this controlled synthesis of cysteine is believed to be the fact that cysteine is a feedback inhibitor of its own synthesis from methionine. While alcohol inhibits the normal intestinal uptake of methionine from the diet, this inhibition is overcome by the administration of relatively large doses of methionine as contained in the present compositions. The cysteine formed from methionine can trap the toxic free radicals and acetaldehyde. Additionally, the formed cysteine can also be used by the body to form glutathione, a compound of immense importance in protecting tissues from a number of reactive and damaging compounds as shown in FIG. 3.

Alcohol depletes intestinal and liver levels of glutathione, and this action opens the way for the damage of these tissues. The replenishment of glutathione via the cysteine produced from the administered methionine maintains the normal protection of tissues from free radical damage. The administered methionine is also a source for in situ synthesis of cysteine which acts to directly trap acetaldehyde. After ingestion of large doses of alcohol, acetaldehyde levels increase in the liver and subsequently in the circulation. Circulating acetaldehyde can produce a stress-like response by releasing norepinephrine and epinephrine from adrenals, cause facial flushing by dilating peripheral blood vessels, and cause headaches, nausea and vomiting, and a number of other symptoms associated with the ill effects of ingestion of large doses of alcohol. The presence of high levels of acetaldehyde in the blood, liver, and other organs also tends to slow alcohol metabolism. However, if acetaldehyde is "trapped" by cysteine, all of the above mentioned adverse physiologic effects produced by acetaldehhyde can be diminished.

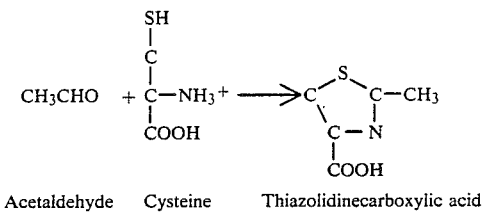

Acetaldehyde   Cysteine   Thiazolidinecarboxylic acid

The preferred single dose range for methionine in order to reduce the blood acetaldehyde level is about 25 mg/kg of body weight to about 100 mg/kg of body weight. Particularly preferred single dose range is about 50 mg/kg.

Potassium citrate can also be present in the compositions of this invention in an amount that provides a single dose of up to about 20 mg/kg, preferably about 4 mg/kg to about 15 mg/kg, and more preferably about 6 mg/kg. The relative amounts of methionine and potassium citrate preferably are in a respective weight ratio of about 1.6 to about 20.

Since Vitamin B6 is an essential constituent in the conversion of methionine to cysteine, the indigenous amount of its physiologically active form, i.e., pyridoxal or a salt thereof, can be supplemented by including a quantity of Vitamin B6 in the present compositions as a further preferred constituent. Vitamin B6 is pyridoxine, and can be incorporated into the present compositions as such or as a physiologically tolerable acid addition salt, for example as pyridoxine hydrochloride, or as the physiologically active form thereof, namely pyridoxal, pyridoxal 5-phosphate, or the like.

The relative amounts of methionine and Vitamin B6 preferably are in a respective weight ratio of about 100 to about 500. Stated in another way, the relative amount of Vitamin B6 administered with respect to methionine preferably is in a respective weight ratio of about 0.01 to about 0.002.

Methionine, the principal active ingredient of the present invention, can be administered perorally or percutaneously in customary dosage unit compositions, that is, as compositions in unit dosage form comprising a physiologically tolerable carrier and an effective dosage unit of the active ingredient.

The preferred amounts of methionine, potassium citrate and Vitamin B6 are set forth in Table I, below.

TABLE I

| Preferred Compositions for Reduction of Blood Acetaldehyde Level | | |
|---|---|---|
| | Preferred Single Dose Range, mg/kg of Body Weight | |
| Compound | Minimum | Maximum |
| methionine | 25 | 100 |
| potassium citrate | 4 | 15 |
| Vitamin B6 | 0.05 | 1 |

The term "unit dosage form" as used herein refers to physically discrete units suitable as unitary dosages for human patients, each unit containing a predetermined quantity of the active ingredient calculated to produce the desired therapeutic effect in association with the required physiologically tolerable carrier, e.g., a diluent or a vehicle. The specifications for the novel unit dosage forms of this invention are dictated by and are directly dependent on (a) the particular therapeutic effect to be achieved, and (b) the limitations inherent in the art of compounding such an active ingredient for its intended therapeutic use in humans. Examples of suitable unit dosage forms in accord with this invention are tablets, capsules, pills, powder packets, granules, wafers, and the like, segregated multiples of any of the foregoing, as well as solutions and suspensions, depending upon the quantity to be administered and patient preference.

Examples of solid pharmaceutical carriers are lactose, maize, starch, dicalcium phosphate, terra alba, sucrose, talc, gelatin, agar, pectin, acacia, magnesium stearate, stearic acid, and the like. Examples of liquid carriers are syrup, peanut oil, olive oil, water, and the like.

For peroral administration, if a solid carrier is used, the amount of solid carrier in a unit dosage form can generally be about 25 milligrams to about 300 milligrams. If a liquid carrier is used, the composition can be in the form of a syrup, emulsion, sterile injectable liquid, an aqueous solution, liquid suspension, and the like. Other additives such as preservatives, e.g., antioxidants, or antibacterials, flavoring agents, coloring agents, and the like can also be included.

The specific amount of active ingredient that is to be administered in a specific case depends also on the age and weight of the patient, the particular condition to be treated, the frequency of administration, and the route of administration. In general, amounts of active ingredients present will fall within the dosage ranges specified hereinabove.

The present invention is further illustrated by the following examples.

EXAMPLE 1

Effects of Methionine on the Production of Toxic Metabolites of Ethanol

Methods

The effects of methionine on circulating levels of acetaldehyde after administration of ethanol to C57B1 mice were monitored. Male mice were used for these experiments.

The mice were given methionine in a quantity of 970 mg/kg body weight. One hour later, the mice received ethanol at a dose of 4.8 g/kg. Both the methionine and the ethanol were administered orally. Control mice were administered a saline solution prior to the administration of ethanol. At predetermined times after the administration of ethanol, blood from the tail was collected and assayed for acetaldehyde by a gas chromatographic technique previously developed (see Tabakoff et al., *Biochem. Pharmacol.* 25:1305, 1976).

Results

Figure 4:
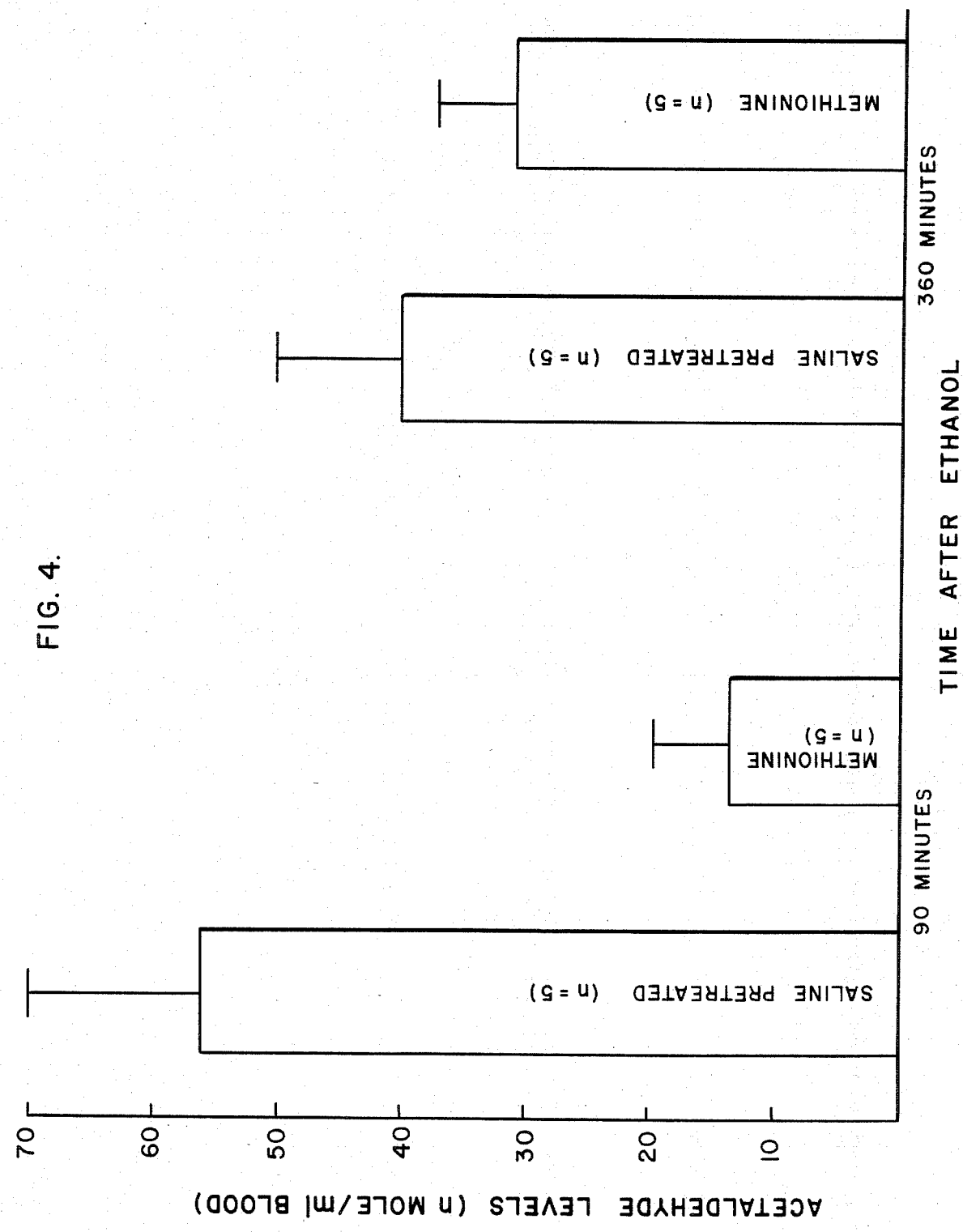
FIG. 4 is a graphical representation presenting a comparison of blood acetaldehyde level reduction in a group of animals given a relatively large dose of alcohol and pretreated with methionine, the results being shown as the mean ± SEM (standard error of the mean) and the value for "n" indicates the number of animals in the group.

The administration of methionine resulted in significant decreases in circulating blood levels of acetaldehyde. The assay results are set forth in FIG. 4.

I claim:

1. A method for reducing elevated blood acetaldehyde level resulting from alcohol ingestion in a patient which consists essentially of administering to the patient an effective amount of methionine prior to alcohol ingestion.

2. The method in accordance with claim 1 wherein the administered amount of methionine is about 25 to about 100 mg/kg of body weight.

3. The method in accordance with claim 1 wherein the administered amount of methionine is about 50 mg/kg of body weight.

4. The method in accordance with claim 1 wherein additionally potassium citrate is administered to the patient in an amount of up to about 20 mg/kg.

5. The method in accordance with claim 4 wherein the amount of potassium citrate administered to the patient is about 4 mg/kg to about 15 mg/kg.

6. The method in accordance with claim 4 wherein the amount of potassium citrate administered to the patient is about 6 mg/kg.

7. The method in accordance with claim 4 wherein additionally Vitamin B6 is administered to the patient in a relative amount with respect to methionine having a weight ratio with respect to methionine of about 0.01 to about 0.002.

8. The method in accordance with claim 1 wherein additionally Vitamin B6 is administered to the patient in a relative amount with respect to methionine having a weight ratio with respect to methionine of about 0.01 to about 0.002.

* * * * *